United States Patent
Mello

(10) Patent No.: US 10,937,148 B2
(45) Date of Patent: Mar. 2, 2021

(54) SYSTEM AND METHOD FOR MONITORING CROPS

(71) Applicant: THE BOEING COMPANY, Chicago, IL (US)

(72) Inventor: Marcio Pupin Mello, San Jose dos Campos (BR)

(73) Assignee: THE BOEING COMPANY, Chicago, IL (US)

( * ) Notice: Subject to any disclaimer, the term of this patent is extended or adjusted under 35 U.S.C. 154(b) by 326 days.

(21) Appl. No.: 15/871,758

(22) Filed: Jan. 15, 2018

(65) Prior Publication Data

US 2019/0220964 A1 Jul. 18, 2019

(51) Int. Cl.

| | |
|---|---|
| G06T 7/00 | (2017.01) |
| A01G 7/00 | (2006.01) |
| A01B 79/00 | (2006.01) |
| B64C 39/02 | (2006.01) |
| G01N 33/24 | (2006.01) |
| A01G 25/16 | (2006.01) |
| A01D 45/10 | (2006.01) |

(52) U.S. Cl.
CPC .......... *G06T 7/001* (2013.01); *A01B 79/005* (2013.01); *A01G 7/00* (2013.01); *B64C 39/024* (2013.01); *G01N 33/24* (2013.01); *A01D 45/10* (2013.01); *A01G 25/167* (2013.01); *B64C 2201/123* (2013.01); *B64C 2201/127* (2013.01); *G01N 2033/245* (2013.01); *G06T 2207/10036* (2013.01); *G06T 2207/30188* (2013.01)

(58) Field of Classification Search
CPC ......... G06T 7/001; A01B 79/005; A01G 7/00; B64C 39/024; G01N 33/24
See application file for complete search history.

(56) References Cited

U.S. PATENT DOCUMENTS 5,467,271 A * 11/1995 Abel .................... A01B 79/005
702/5
6,567,537 B1 * 5/2003 Anderson .......... G06K 9/00657
382/110

(Continued)

OTHER PUBLICATIONS

Corrigan, F. "Multispectral Imaging Camera Drones in Farming Yield Big Benefits," DroneZon, Oct. 20, 2017, <https://www.dronezon.com/learn-about-drones-quadcopters/multispectral-sensor-drones-in-farming-yield-big-benefits/>, 16 pgs.

*Primary Examiner* — Vincent Rudolph
*Assistant Examiner* — Raphael Schwartz
(74) *Attorney, Agent, or Firm* — Moore IP Law

(57) ABSTRACT

A system includes an aerial sensor platform including a spectral imaging device, a position sensor, and an orientation sensor and includes a ground-based sensor platform including at least one soil sensor. The system also includes a computing device with instructions that are executable by a processor to obtain spectral imaging data collected by the spectral imaging device and soil data collected by the at least one soil sensor. The spectral imaging data represents a particular field of view (based on data from the orientation sensor) of a particular geographic region (based on data from the position sensor) of a crop field and the at least one soil sensor is associated with the particular geographic region. The instructions are further executable by the processor to schedule an agricultural activity based on the spectral imaging data and the soil data.

20 Claims, 7 Drawing Sheets

(56) References Cited

U.S. PATENT DOCUMENTS

| | | | |
|---|---|---|---|
| 2007/0039745 A1* | 2/2007 | Anderson | A01B 79/005 172/6 |
| 2015/0347647 A1* | 12/2015 | Osborne | B09C 1/002 703/6 |
| 2016/0300363 A1* | 10/2016 | Young | G06T 7/11 |
| 2017/0096222 A1 | 4/2017 | Spinelli et al. | |
| 2017/0118925 A1* | 5/2017 | Noguchi | G06Q 50/02 |
| 2017/0223947 A1* | 8/2017 | Gall | G01N 21/4738 |

\* cited by examiner

SYSTEM AND METHOD FOR MONITORING CROPS

FIELD OF THE DISCLOSURE

The present disclosure is generally related to systems and methods of monitoring crops, especially biofuel feedstock crops.

BACKGROUND

Many individuals, companies, and even nations have set ambitious goals to reduce their environmental impact by switching to sustainably produced biofuels. For example, some have cited sustainable biofuels as the most suitable power source to replace fossil-based jet fuels in the next decades. By some estimates, when produced sustainably, aviation biofuels may reduce carbon emissions throughout their lifecycle by 50% to 80% as compared to petroleum derived jet fuel. A well-established aviation biofuel industry would reduce the aviation industries' reliance on petroleum.

Quantifying the environmental benefit due to use of biofuels entails quantifying emissions during all stages of crop production, processing of feedstock to biofuel, and biofuel use. While processing and use of biofuels are relatively easy to quantify, it can be challenging to quantify emissions due to crop production. The quality and usefulness of field studies are often compromised when data from multiple sources, collected at different times (e.g. year, month, time of day) and in different conditions (e.g. drought, rain, and snow) are combined. This is especially true when field studies are time sensitive, such as tracking the rise and fall of floods and their effects, tracking the long term effects of drought, or the longer term effects of climate change in temperature sensitive locations (e.g., glacial fields).

SUMMARY

In a particular implementation, an agricultural monitoring system includes an aerial sensor platform and a ground-based sensor platform. The aerial sensor platform includes a spectral imaging device, a position sensor, and an orientation sensor. The ground-based sensor platform includes at least one soil sensor. The agricultural monitoring system also includes a computing device including a processor and a memory storing instructions. The instructions are executable by the processor to obtain spectral imaging data collected by the spectral imaging device. The spectral imaging data represents a particular field of view of a particular geographic region of a crop field, where the particular geographic region is determined based on position data from the position sensor and the particular field of view is determined based on orientation data from the orientation sensor. The instructions are further executable by the processor to obtain soil data collected by the at least one soil sensor, where the at least one soil sensor associated with the particular geographic region. The instructions are further executable by the processor to schedule an agricultural activity based on the spectral imaging data and the soil data.

In another particular implementation, a method for monitoring biofuel feedstock crops includes obtaining multiple images, each image of the multiple images collected by a spectral imaging device of an aerial sensor platform during a particular sampling period. The multiple images include a first image representing a first field of view of a first geographic region of a crop field and include a second image representing a second field of view of a second geographic region of the crop field. The method also includes obtaining soil data collected by multiple ground-based sensor platforms during the particular sampling period. The soil data includes first soil data associated with the first geographic region and second soil data associated with the second geographic region. The method further includes obtaining historical data associated with the crop field and analyzing chemical spectra of the multiple images, the soil data, and the historical data to project a state of the crop field at a time subsequent to the particular sampling period. The method also includes generating and storing, based on the projected state of the crop field, a schedule entry, where the schedule entry schedules an agricultural activity at the crop field.

In another particular implementation, an agricultural monitoring system includes a transmitter, a receiver, and a data collection controller coupled to the transmitter and to the receiver. The data collection controller includes a processor and a memory, and the memory stores instructions. The instructions are executable by the processor to cause the data collection controller to cause the transmitter to transmit, to an aerial sensor platform and to a ground-based sensor platform, at least one signal to synchronize data collection by a spectral imaging device of the aerial sensor platform and by a soil sensor of the ground-based sensor platform. The instructions are also executable by the processor to cause the data collection controller to receive, via the receiver and responsive to the at least one signal, spectral imaging data from the aerial sensor platform. The spectral imaging data represents a particular field of view of a particular geographic region of a crop field, where the particular geographic region is determined based on position data from a position sensor of the aerial sensor platform and the particular field of view is determined based on orientation data from an orientation sensor of the aerial sensor platform. The instructions are further executable by the processor to cause the data collection controller to receive, via the receiver and responsive to the at least one signal, soil data from the ground-based sensor platform, where the soil data is associated with the particular geographic region. The instructions are also executable by the processor to cause the data collection controller to generate a set of synchronized sample data including the soil data and the spectral image data and store the set of synchronized sample data in the memory.

DETAILED DESCRIPTION

Figure 1:
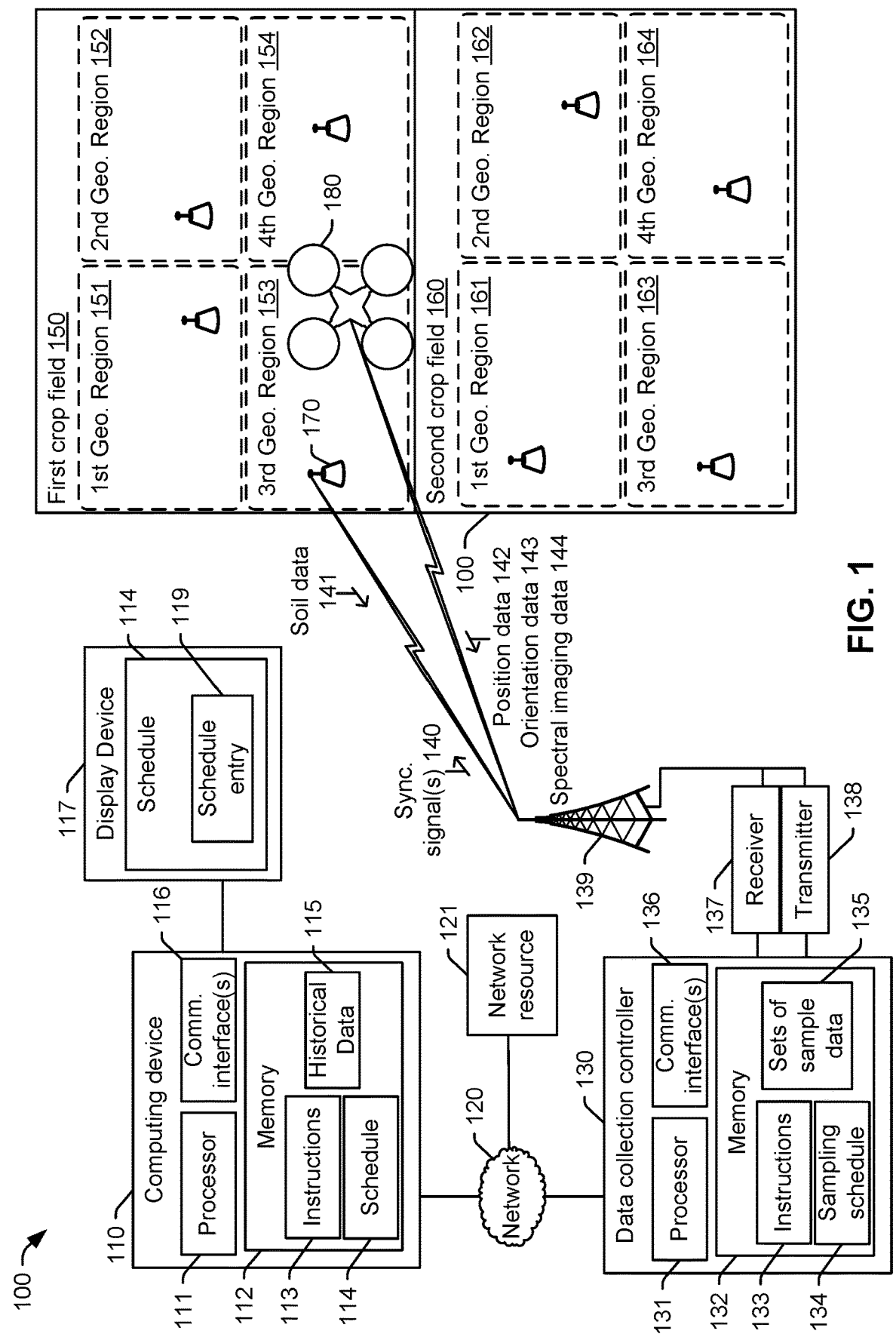
FIG. 1 is a block diagram that illustrates an agricultural monitoring system according to a particular implementation.

Particular implementations are described with reference to the drawings. In the description, common features are designated by common reference numbers throughout the drawings. As used herein, various terminology is used for the purpose of describing particular implementations only and is not intended to be limiting. For example, the singular forms "a," "an," and "the" are intended to include the plural forms as well, unless the context clearly indicates otherwise. Further, the terms "comprise," "comprises," and "comprising" are used interchangeably with "include," "includes," or "including." Additionally, the term "wherein" is used interchangeably with "where." As used herein, "exemplary" may indicate an example, an implementation, and/or an aspect, and should not be construed as limiting or as indicating a preference or a preferred implementation. As used herein, an ordinal term (e.g., "first," "second," "third," etc.) used to modify an element, such as a structure, a component, an operation, etc., does not by itself indicate any priority or order of the element with respect to another element, but rather merely distinguishes the element from another element having a same name (but for use of the ordinal term). As used herein, the term "set" refers to a grouping of one or more elements, and the term "plurality" refers to multiple elements.

In the present disclosure, terms such as "determining", "calculating", "generating", "adjusting", "modifying", etc. may be used to describe how one or more operations are performed. Such terms are not to be construed as limiting and other techniques may be utilized to perform similar operations. Additionally, as referred to herein, "generating", "calculating", "using", "selecting", "accessing", and "determining" may be used interchangeably. For example, "generating", "calculating", or "determining" a parameter (or a signal) refers to actively generating, calculating, or determining the parameter (or the signal) or refers to using, selecting, or accessing the parameter (or signal) that is already generated, such as by another component or device. Additionally, "adjusting" and "modifying" may be used interchangeably. For example, "adjusting" or "modifying" a parameter can refer to changing the parameter from a first value to a second value (a "modified value" or an "adjusted value"). As used herein, "coupled" includes "communicatively coupled," "electrically coupled," "physically coupled," or any combinations thereof. Two devices (or components) may be coupled (e.g., communicatively coupled, electrically coupled, or physically coupled) directly or indirectly via one or more other devices, components, wires, buses, networks (e.g., a wired network, a wireless network, or a combination thereof), etc. Two devices (or components) that are electrically coupled can be included in the same device or in different devices and can be connected via electronics, one or more connectors, or inductive coupling, as illustrative, non-limiting examples. In some implementations, two devices (or components) that are communicatively coupled, such as in electrical communication, send and receive electrical signals (digital signals or analog signals) directly or indirectly, such as via one or more wires, buses, networks, etc. As used herein, "directly coupled" refers to two devices that are coupled (e.g., communicatively coupled, electrically coupled, or physically coupled) without intervening components.

Implementations disclosed herein enable monitoring of crops, such as biofuel feedstock crops or other crops. Data gathered through monitoring can be used to quantify environmental impacts of producing crops used as biofuel feedstock. Additionally, the data can be used to schedule agricultural activities, such as planting, irrigating, and harvesting. Using data gathered by an agricultural monitoring system as described herein may enable controlling agricultural activities to reduce a net environmental impact of the biofuels. Additionally, or in the alternative, using data gathered by the agricultural monitoring system described herein can enable improved scheduling of agricultural activities. For example, harvesting can be scheduled based on measured chemical content (e.g., a quantity of a biofuel precursor chemical) of a crop, projected future chemical content of the crop, and availability of harvesting resources. As a specific example, if two fields in an area are both growing a biofuel feedstock crop and both are approaching harvest time, a rate of increase of a target chemical (e.g., a sugar) in each crop can be compared, based on chemical spectra gathered using the agricultural monitoring system described herein, to determine which of the two fields to harvest first. In this example, a field in which the rate of increase of the target chemical is lower may be harvest first since this strategy will enable the other field to continue producing the target chemical at the higher rate.

One viable source of biofuel is ethanol derived from various sugars in sugarcane. With the advent of flex-fuel cars (with engines that can run on blends of gasoline and ethanol), interest in growing sugarcane for ethanol production has increased in sugarcane-producing areas over the last decade. For example, according to some statistics, Brazil had more than 10 million hectares planted in sugarcane in 2016. In tropical environments, such as Brazil, production of sugarcane often follows a cycle. For example, a field freshly planted in sugarcane may remain for about 18 month before being harvested. During the first several months (e.g., from January to March), the sugarcane plants grow and flourish in hot and humid conditions. Subsequently, the plants rest through a dry season (e.g., April through August) and develop with high intensity in the following months (e.g., September to April) before being harvested. After about 18 months, the sugarcane is harvested, and the crop is allowed to regrow for about 12 months before being harvested again. This process of harvest and regrowth can be repeated for a number of years (e.g., 5-7 years) depending, for example, on the sugarcane variety, soil conditions, weather, etc. After a number of such harvest and regrowth cycles (e.g., six), the field is "renovated" by replanting the field with a different crop, such as a leguminous crop, that is used to put the nitrogen back into the soil and to balance soil chemistry and physical soil conditions. After renovation, sugarcane is again planted in the field and a new set of harvest and regrowth cycles begins.

Using the above sugarcane growth process as an example, the agriculture monitoring system described herein can improve crop yield (in terms of specific chemical constituents if desired), reduce costs, and reduce net environmental impact by scheduling agricultural activities based on data gathered using careful techniques that improve data quality and allow historical trends to be identified and used to project future conditions. Additionally, the agricultural monitoring system enables automation of some agricultural activities, such as irrigation, pest control, or even harvesting.

In various aspects, the agricultural monitoring system enables simultaneous data collection of multiple different types of data related to a crop or a crop field. For example, data for a particular field (whether planted or awaiting planting) can be gathered simultaneously from ground-based sensors and aerial sensors. The data can be aggregated with other information that indicates, for example, a data collection time, data collection coordinates, orientation of imaging systems during data collection, ambient conditions (e.g., solar angle, temperature, humidity), other information, or a combination thereof. The data can also be aggregated with data gathered from other sources, such as geological or geographic information descriptive of the field, hydrological information descriptive of the field, meteorological data, etc. In some implementations, the agricultural monitoring system includes a data collection controller that facilitates synchronized collection of data and that controls data collection to provide repeatable sampling operations. By gathering data using carefully controlled and repeatable sampling operations over a wide geographic region and through several crop cycles, historical data can be accumulated to enable projecting future conditions based on sampled conditions, which enables optimizing or improving scheduling of agricultural activities.

In particular implementations, as a crop grows, the agriculture monitoring system can measure chemical and physical parameters of the crop using low-altitude aerial sensors. Additionally, soil parameters can be simultaneously measures using ground-based sensors. Data gathered by these sensors enables identification of or detection of, for example: weed plants, gaps in the crop (e.g., areas of low crop density), crop height, indicators of water stress, presence of harmful organisms or infections, crop variety, soil chemical and physical conditions, or combinations thereof. Based on such data, various agricultural activities can be scheduled or automatically performed. For example, harvesting of a field can be scheduled to coincide with availability of harvesting equipment, a peak in a rate of production of a target chemical (e.g., a sugar) by the crop, and a weather forecast prediction indicating of favorable harvesting weather. As another example, a particular field of a set of fields can be scheduled to be planted with a nitrogen-fixing crop before another field based on soil nitrogen conditions of the fields, historical or current production rates of the fields, etc. Other factors may also, or in the alternative, be used to schedule the agricultural activities. Further, other agricultural activities can be scheduled, such as irrigation, fertilization, or control of harmful organisms (e.g., pest animals or weeds). Data collection and some scheduled agricultural activities can be automated and controlled by the agricultural monitoring system. For example, selective irrigation of a field or set of fields can be controlled agricultural monitoring system.

FIG. 1 is a block diagram that illustrates an agricultural monitoring system 100 according to a particular implementation. The agricultural monitoring system 100 is configured to monitor (e.g., gather data related to) one or more crop fields, such as a first crop field 150 and a second crop field 160. In this context, a "crop field" refers to a portion of land that is either planted in a crop or is planned for use to plant a crop. Thus, the term crop field does not imply that a crop is present; rather, the term includes fields designated for agricultural use before a crop is planted, while a crop is growing, and/or after the crop is harvested.

While FIG. 1 illustrates two crop fields 150, 160, in some implementations, the agricultural monitoring system 100 can be used to monitor a single crop field or to monitor more than two crop fields. Further, each crop field 150, 160 can include more than one sampling region. For example, in FIG. 1, the first crop field 150 includes a first geographic region 151, a second geographic region 152, a third geographic region 153, and a fourth geographic region 154. Also in FIG. 1, the second crop field 160 includes a first geographic region 161, a second geographic region 162, a third geographic region 163, and a fourth geographic region 164.

In some implementations, each geographic region of each crop field includes one or more ground-based sensor platforms, such as a ground-based sensor platform 170 of the third geographic region 153 of the first crop field 150. While only one ground-based sensor platform is shown in each geographic region in FIG. 1, in other implementations, one or more geographic regions can include more than one ground-based sensor platform. The ground-based sensor platforms includes sensors to gather soil data, data specific to the particular geographic region (such as local ambient temperature, local rainfall, etc.), or a combination thereof. To illustrate, in some implementations, each of the ground-based sensor platforms includes a soil composition sensor, a soil nitrogen sensor, a soil pH sensor, a soil moisture sensor, a soil temperature sensor, a soil conductivity sensor, or a combination thereof. The ground-based sensor platforms are described in further detail with reference to FIG. 3.

The agricultural monitoring system 100 also includes one or more aerial sensor platforms, such as an aerial sensor platform 180. Each aerial sensor platform is an aircraft (e.g., an unmanned aerial vehicle (UAV)) that is configured to move from one sampling position to another sampling position to gather data. For example, while FIG. 1 shows the aerial sensor platform 180 in the third geographic region 153 of the first crop field 150 during a particular data collection period, the aerial sensor platform 180 may gather data in another geographic region 151, 152, 154 of the first crop field 150 or in the second crop field 160 during a different data collection period. The aerial sensor platform 180 can be self-piloted (e.g., based on instructions stored in a memory of the aerial sensor platform 180) or can be piloted remotely (e.g., via transmissions from a data collection controller 130).

The aerial sensor platform 180 includes sensors to gather crop data or data related to a larger geographic area than can be sampled by a ground-based sensor platform. To illustrate, in some implementations, the aerial sensor platform 180 includes a spectral imaging device, such as a multi-spectral imaging device or a hyperspectral imaging device, configured to gather spectral imaging data representing a particular field of view of a particular geographic region of a crop field. In this example, the spectral imaging data can be analyzed to identify particular chemical compounds (e.g., using spectral analysis), to identify particular plant species (e.g., using object recognition to detect leaf shape and color), to detect or identify pest animals (e.g., using object recognition), and for other purposes. In some implementations, the aerial sensor platform 180 includes a plant height sensor. For example, plant height can be sensed using a light detection and ranging (LIDAR) system. The aerial sensor platform 180 also includes a position sensor (such as a global positioning system receiver, a local position system receiver, or a dead reckoning system). The position sensor generates position data indicating where the aerial sensor platform 180 is to facilitate capturing data from the same sampling positions over time (e.g., from one data collection period to another), which makes identifying trends simpler and more reliable. The aerial sensor platform 180 also includes an orientation sensor (such as one or more gyroscopic or acceleration-based systems). The orientation sensor generates orientation data indicating a pointing direction of the spectral imaging device of the aerial sensor platform 180. The pointing direction of the spectral imaging device indicates a field of view of the spectral imaging device, and the orientation data facilitates capturing data from the field of view over time (e.g., from one data collection period to another), which also makes identifying trends simpler and more reliable. Additional detail regarding the aerial sensor platform 180 is provided with reference to FIG. 2. In some implementations, the aerial sensor platform 180 also includes other sensors, such as a light meter, a temperature sensor, a humidity sensor, a barometric pressure sensor, or a combination thereof.

In FIG. 1, the agricultural monitoring system 100 also includes the data collection controller 130 and a computing device 110. The data collection controller 130 includes a processor 131, a memory 132, and one or more communication interfaces 136. The memory 132 stores instructions 133 that are executable by the processor 131 to cause the data collection controller 130 to perform the various operations described herein. The memory 132 may also store a sampling schedule 134 that includes information to facilitate consistent data collection. For example, the sampling schedule 134 can indicate times and locations for data collection. The memory 132 may also store sets of sample data 135, described further below, which may be provided to the computing device 110 for analysis.

The computing device 110 includes a processor 111, a memory 112, and one or more communication interfaces 116. The memory 112 stores instructions 113 that are executable by the processor 111 to cause the computing device 110 to perform the various operations described herein. The memory 112 also stores a schedule 114 that indicates agricultural activates to be performed at various crop fields 150, 160 or various geographic regions 151-154, 161-164 of the crop fields 150, 160. In some implementations, the memory 112 also stored historical data 115 that is used to identify trends, to predict future states of the crop fields 150, 160, etc. In other implementations, the historical data 115 is stored at a separate memory, such as at a memory of a network resource 121. Additional detail regarding analyzing the sets of sample data 135 and generating the schedule 114 is provided with reference to FIGS. 5 and 6.

In the example illustrated in FIG. 1, the computing device 110 is separate from the data collection controller 130 and communicates with the data collection controller via a network 120. In other implementations, the computing device 110 is integrated with the data collection controller 130.

The data collection controller 130 is configured to synchronize data collection by the sensor platforms (including the aerial sensor platforms and the ground-based sensor platforms). For example, in FIG. 1, the data collection controller 130 is coupled to a transmitter 138, which is coupled to an antenna 139. In this example, the data collection controller 130 causes the transmitter 138 to send synchronization signals 140 via a radio-frequency transmission. The sensor platforms are configured to gather data using various sensors in response to the synchronization signals 140. In some implementations, the synchronization signals 140 are broadcast signals (e.g., are not addressed to particular sensor platforms) in which case all of the sensors platforms that receive the synchronization signals 140 generate sample data based on the synchronization signals 140. To illustrate, in such implementations, the synchronization signals 140 can include periodic or scheduled signals that cause all of the sensor platforms to gather data at regular intervals or at particular times of day, days of the week, etc. In other implementations, the synchronization signals 140 are unicast or multicast signals (e.g., are addressed to a particular subset of the sensor platforms) in which case the addressed sensors platforms generate sample data based on the synchronization signals 140. To illustrate, in such implementations, the synchronization signals 140 can be transmitted based on determining that the aerial sensor platform 180 is at a sampling location, such as near the ground-based sensor platform 170, and the synchronization signals 140 can cause the aerial sensor platform 180 and the ground-based sensor platform 170 to sample data substantially simultaneously.

Data gathered by the sensor platforms is conveyed to the data collection controller 130, which aggregates the data into related data sets (e.g., the sets of sample data 135). For example, a set of sample data of the sets of sample data 135 can include data gathered from a portion of a particular crop field during a particular data collection period. In some implementations, a set of sample data also includes data gathered from other sources, such as the network resource 121. In such implementations, the network resource 121 can provide, for example, meteorological data (e.g., temperature, humidity, wind speed, wind direction, rainfall) regarding a geographic region that includes the particular crop field, geological data (e.g., soil type, terrain) regarding the geographic region, hydrological data (e.g., ground-water table level) regarding the geographic region, astronomical data (e.g., solar angle) regarding the particular data collection period, or a combination thereof.

In the example illustrated in FIG. 1, after generating sample data, the sensor platforms transmit the sample data to the data collection controller 130 via a wireless transmission. In this example, the data collection controller 130 is coupled to a receiver 137 that receives the sample data via the antenna 139 and provides the sample data to the data collection controller 130. In other examples, the sample data is provided to the data collection controller 130 using other techniques. For example, the aerial sensor platform 180 can store sample data that it collects at a local memory and connect, via a physical link, to the data collection controller 130 to download the sample data after sampling several locations. In this example, the ground-based sensor platform 170 can wirelessly transmit its sample data or can be connected to the data collection controller 130 via a wired connection to download the sample data.

During operation, the data collection controller 130 determines when to initiate data gathering based on the sampling schedule 134. In some implementations, the sampling schedule 134 indicates when to initiate a data collection period based on time. To illustrate, a data collection period can be initiated based on a time elapsed since previous samples were gathered, based on a current date or current time corresponding to the beginning of a data collection period, or a combination thereof. Additionally or in the alternative, the sampling schedule 134 can indicate when to initiate a data collection period based on information received from the sensor platforms. For example, the sampling schedule 134 can indicate that a data collection period is to be initiated responsive to an indication that that aerial sensor platform 180 is ready to gather sample data (e.g., is at a particular position based on position data 142 and has a particular field of view based on orientation data 143). Additionally or in the alternative, the data collection controller 130 can determine the sampling schedule 134 based on conditions that change over time. For example, the data collection controller 130 can schedule a particular data collection period when relevant ambient conditions are similar to ambient conditions present during previous data collection periods to make comparing the data collected during different data collection periods simpler. To illustrate, solar angle can change ambient lighting conditions sufficiently that it can be difficult to compare two spectral images that are collected at the same time of day and the same location but during different seasons. In this illustration, the data collection controller 130 can schedule data collection periods based on solar angle information, as described further with references to FIGS. 4A-4D. Combinations of the above techniques can also be used. To illustrate, the sampling schedule 134 can indicate that data collection should occur in the third geographic regions 153 of the first crop field 150 between 9 a.m. and 11 a.m. on a particular date (based on the solar angle during that time range and on the particular date), and as soon after 9 a.m. as the position data 142 and the orientation data 143 indicate that the aerial sensor platform 180 is in position.

To initiate data gathering, the data collection controller 130 causes the transmitter 138 to transmit the synchronization signals 140. Responsive to the synchronization signals 140 the aerial sensor platform 180 and at least one of the ground-based sensor platforms (e.g., the ground-based sensor platform 170) capture data substantially simultaneously or concurrently. Since the data changes relatively gradually over the course of a day or even a season, exact simultaneity is not essential. Thus, "substantially simultaneous" should be understood to include a reasonable time period over which the data is unlikely to change, such as within several minutes (e.g., 1 to 2 minutes) of each other.

In the example illustrated in FIG. 1, the ground-based sensor platform 170 wirelessly transmits the soil data 141 collected responsive to the synchronization signals 140 to the data collection controller 130. Additionally, the aerial sensor platform 180 wirelessly transmits spectral imaging data 144 collected responsive to the synchronization signals 140 to the data collection controller 130. The spectral imaging data 144 includes one or more images (also referred to herein as "spectral images" to indicate that the spectrum data of the images is retained) or data representative of one or more images. The data collection controller 130 aggregates the soil data 141, the spectral imaging data 144, and possibly other data to generate a set of synchronized sample data and stores the set of synchronized sample data as an entry in the sets of sample data 135 in the memory 132. The data collection controller 130 provides the set of synchronized sample data (and possibly other sets of sample data 135) to the computing device 110. For example, during a first data collection period, the data collection controller 130 may cause the transmitter 138 to transmit first synchronization signals, and the receiver 137 may receive first soil data and first spectral imaging data from the sensor platforms in response to the first synchronization signals. Subsequently, during a second data collection period, the data collection controller 130 may cause the transmitter 138 to transmit second synchronization signals, and the receiver 137 may receive second soil data and second spectral imaging data from the sensor platforms in response to the second synchronization signals. In this example, the data collection controller 130 generates a first set of synchronized sample data based on the first soil data and the first spectral imaging data and generates a second set of synchronized sample data based on the second soil data and the second spectral imaging data. The first set of synchronized sample data and the second set of synchronized sample data may each include information indicating a date and time of data capture and a location of each sensor that captured data in the set.

The computing device 110 analyzes the set of synchronized sampling data (and possibly other data) to generate a schedule entry 119 of the schedule 114. The computing device 110 stores the schedule entry 119 in the memory 112 as part of the schedule 114, and may also display the schedule 114 or the schedule entry 119 to a user via a display device 117. In some implementations, the computing device 110 automatically initiates an agricultural activity based on the schedule 114 or the schedule entry 119. For example, the computing device 110 may send a control signal to an irrigation system (not shown) to initiate irrigation of a portion of one of the crop fields 150, 160.

As a specific example, the computing device 110 can obtain, from a particular set of sample data, the spectral imaging data 144, where the spectral imaging data 144 represents a particular field of view (based on the orientation data 143) of a particular geographic region (based on the position data 142) of a crop field. In this example, the computing device 110 can also obtain, from the particular set of sample data, the soil data 141, where the soil data 141 is also associated with the particular geographic region. Based on the spectral imaging data 144, the computing device 110 can estimate a current biochemical content associated with the crop field. For example, the spectral imaging data 144 can be analyzed to estimate a quantity of a target chemical (such as a sugar) represented in chemical spectra of the spectral imaging data 144. The computing device 110 can also project a future biochemical content associated with the crop field based on the current biochemical content, the soil data 141, and the historical data 115. For example, the historical data 115 can be analyzed to identify a historical trend that indicates a particular growth rate or a particular chemical constituent change rate (e.g., a ripening rate) experienced by the crop field or similar crop fields under particular circumstances, such as with particular soil nitrogen content levels, particular soil water content, etc. Based on the future biochemical content, the computing device 110 can determine a harvest date range. To illustrate, the harvest date range may correspond to a range of several days or several weeks when a peak rate of increase of the chemical constituent is reached or has just passed. A harvesting agricultural activity can be scheduled to correspond to a date within the harvest date range.

As another specific example, after the computing device 110 obtains the spectral imaging data 144 and the soil data 141 from a particular set of sample data, the computing device 110 can also obtain, from a second particular set of sample data, second spectral imaging data representing a second crop field and second soil data associated with the second crop field. In this example, the computing device 110 can prioritizing planting or harvesting of one of the crop fields ahead of planting or harvesting of the other of the crop fields. Alternatively or in addition, the computing device 110 can schedule planting of a particular crop (among a plurality of candidate crops) in one or both of the crop fields. For example, the spectral imaging data and the soil data can be used to determine nitrogen concentrations in two or more crop fields. In this example, a crop field with a lowest nitrogen concentration can be scheduled for renovation by planting a nitrogen fixing crop. In one exemplary embodiment, the agricultural monitoring system can estimate a harvest date range for a crop field of a specific sugar cane variety, based on the collected sensor data, analysis of prior growth rates and the sensed crop height, which may be a height of at least 2 meters, for example. In the exemplary embodiment, the crop may be a sugar cane variety such as RB 835486, RB 855536 or RB 855453, for example.

Thus, the agricultural monitoring system 100 enables automatic analysis of data related to crop fields and scheduling of particular agricultural activates based on the analysis. In some implementations, the agricultural monitoring system 100 can also automatically initiate certain of the agricultural activates, such as irrigation, fertilization, or pest control.

Figure 2:
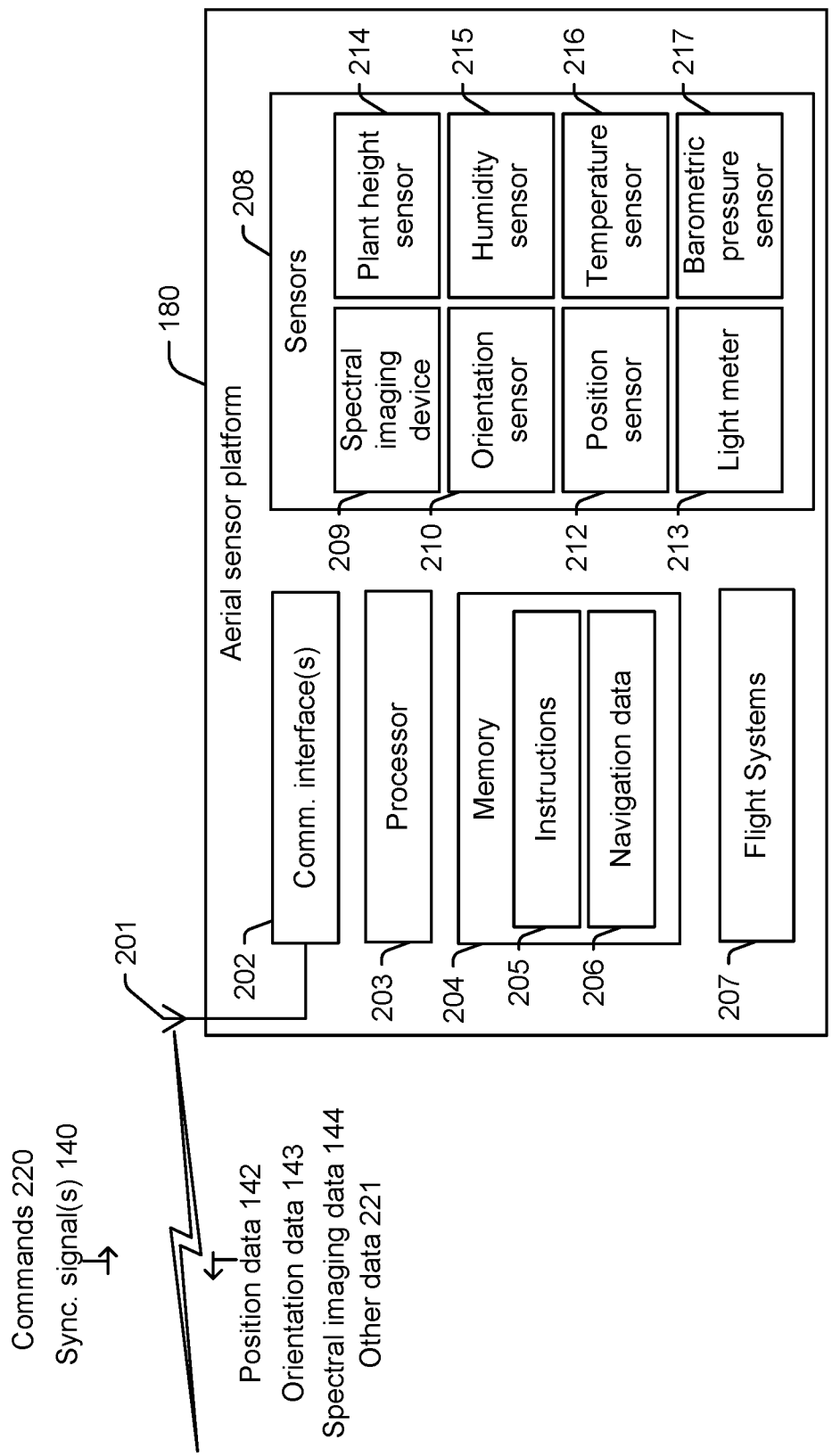
FIG. 2 is a block diagram that illustrates an aerial sensor platform of the agricultural monitoring system of FIG. 1.

FIG. 2 is a block diagram that illustrates an example of the aerial sensor platform 180 in further detail. In the example illustrated in FIG. 2, the aerial sensor platform 180 includes a processor 203, a memory 204, flight systems 207, a plurality of sensors 208, and one or more communication interfaces 202. In FIG. 2, the communication interfaces 202 include a wireless communication interface (e.g., including a transmitter and a receiver) coupled to an antenna 201. The communications interfaces 202 can also include a wired communication interface, such as a data port (e.g., a universal serial bus (USB) port, an Ethernet port, etc.).

The processor 203 is configured to execute instructions 205 stored in the memory 204 to control operation of the aerial sensor platform 180. In some implementations, the processor 203 is also configured to perform one or more operations responsive to the synchronization signals 140 and commands 220 received via the communications interfaces 202. For example, the commands 220 can include flight control commands (e.g., remote piloting input) from the data collection controller 130 or navigational commands (e.g., waypoints) to direct the aerial sensor platform 180 to a geographic region to collect data. In this example, the processor 203 controls the flight systems 207 based on the commands 220 to move the aerial sensor platform 180 at a particular position to gather data. As another example, the commands 220 can direct that particular ones of the sensors 208 be used to gather data. For example, the commands 220 may direct that, at a particular sampling position, a spectral imaging device 209, a plant height sensor 214, and a temperature sensor 216 be used to gather data.

The instructions 205 are executable by the processor 203 to control various subsystems of the aerial sensor platform 180. For example, the instructions 205 include one or more communication protocol stacks to enable the processor 203 to send and receive information via the communications interfaces 202. The instructions 205 also include flight instructions that are executable by the processor 203 to control the flight systems 207 to navigate the aerial sensor platform 180, to stabilize the aerial sensor platform 180, etc. In some implementations, one or more of the sensors 208 provide data to the processor 203 for use in controlling flight of the aerial sensor platform 180. To illustrate, the sensors 208 can include a position sensor 212 and an orientation sensor 210. In this example, the position sensor 212 can include a global positioning system receiver, a local positioning system receiver, or a dead reckoning system that generates the position data 142. In addition to, or instead of, being transmitted to the data collection controller 130, the position data 142 can be provided to the processor 203, which can compare the position data 142 to a waypoint or sample position indicated in the navigation data 206 to determine a flight path of the aerial sensor platform 180. The orientation data 143 from the orientation sensor 210 can also be provided to the processor 203 as flight control feedback (e.g., indicating a pitch, roll, or yaw of the aerial sensor platform 180 during flight), to facilitate determination of a field of view of the spectral imaging device 209, or both.

The flight systems 207 include components to generate thrust and lift and components to enable flight path control. The specific components of the flight systems 207 are different in different implementations. For example, in some implementations the aerial sensor platform 180 is a rotary-wing aircraft. In such implementations, the flight systems 207 include a plurality of rotors that provide lift, thrust, and flight path control. To illustrate, in a quadcopter implementation, four rotors and corresponding motors are be used to provide lift, thrust, and flight path control. In other implementations, the aerial sensor platform is a fixed wing aircraft. In such implementations, the flight systems 207 include one or more propellers, fans, or jets to provide thrust, wings to provide lift, and flight surfaces or wing deformation actuators to provide flight path control. In yet other implementations, the aerial sensor platform is a lighter-than-air aircraft. In such implementations, flight systems 207 include a buoyant body (e.g., a bladder or balloon) and a low-density gas to provide lift, one or more propellers, fans, or jets to provide thrust. In such implementations, flight path control can be provided by the one or more propellers, fans, or jets that provide thrust, or can be provided by separate flight control surfaces. Hybrids of the above implementations are also possible, such as an aircraft that includes a buoyant body to provide some lift and one or more rotors, wings, or lifting body shapes to provide additional lift.

In FIG. 2, the sensors 208 include the spectral imaging device 209, the orientation sensor 210, the position sensor 212, a light meter 213, the plant height sensor 214, a humidity sensor 215, the temperature sensor 216, and a barometric pressure sensor 217. In other implementations, the sensors 208 include more sensors, fewer sensors, or different sensors.

The spectral imaging device 209 includes an image sensor configured to capture the spectral imaging data 144. In a particular implementation, the spectral imaging device 209 can include filters or data processing components such that spectral imaging data 144 corresponds to single, relatively narrow wavelength of the electromagnetic spectrum. In this implementation, the spectral imaging data 144 can include a single spectrum image, e.g., an image corresponding to the single, narrow wavelength. For example, the single, narrow wavelength of the single spectrum image may correspond to a near-infrared wavelength selected to enable detection of pest animals based on body heat. In other implementations, the spectral imaging device 209 can include filters or data processing components such that spectral imaging data 144 corresponds to multiple non-adjacent sets of wavelengths of the electromagnetic spectrum. In this implementation, the spectral imaging device 209 corresponds to or includes a multispectral image sensor, and the spectral imaging data 144 includes a multispectral image, e.g., an image corresponding to the multiple non-adjacent sets of wavelengths. For example, the multiple non-adjacent sets of wavelengths may correspond to a near-infrared wavelength selected to enable detection of pest animals based on body heat and one or more emission peak wavelengths associated with particular target chemicals. In other implementations, the spectral imaging device 209 can include filters or data processing components such that spectral imaging data 144 corresponds to multiple adjacent sets of wavelengths of the electromagnetic spectrum. In this implementation, the spectral imaging device 209 can correspond to or include a hyperspectral image sensor, and the spectral imaging data 144 can include a hyperspectral image, e.g., an image corresponding to a wide range of adjacent wavelengths including and extending beyond a visible wavelength range of humans. In still other implementations, the spectral imaging device 209 can include filters or data processing components such that spectral imaging data 144 corresponds approximately to a visible wavelength range of humans. Although FIG. 2 illustrates a single spectral imaging device 209, in some implementations, the aerial sensor platform 180 includes more than one spectral imaging device 209. In such implementations, the processor 203 can control the multiple spectral imaging devices to synchronize image capture by the spectral imaging devices. For example, in such an implementation, the spectral imaging data 144 can include multiple synchronously captured images corresponding to different (though possibly overlapping or partially overlapping) wavelength ranges.

The orientation sensor 210 includes sensors to determine an orientation of the aerial sensor platform 180 in space, such as a pitch angle, a yaw angle, and a roll angle. For example, the orientation sensor 210 can include a plurality of gyroscopic sensors. The orientation sensor 210 generates the orientation data 143 which can be used, with the position data 142, to determine a field of view of the spectral imaging device 209 to ensure that the spectral imaging data 144 corresponds to an image of a target field of view.

The light meter 213 includes circuitry to generate an output based on light reflected by a scene corresponding to a field of view of the spectral imaging device 209. The light meter 213 may provide a signal to the processor 203, to the spectral imaging device 209, or to both. If the spectral imaging device 209 includes a filter or data processing system configured to exclude particular wavelengths of the electromagnetic spectrum, the light meter 213 may also be configured to exclude the particular wavelengths so that the light meter 213 detects the same wavelength or wavelengths used to generate the spectral imaging data 144. In implementations in which the aerial sensor platform 180 includes multiple spectral imaging devices 209 corresponding to multiple different wavelength ranges, the aerial sensor platform 180 can also include more than one light meter 213, with each of the light meters 213 configured to detect light in a wavelength range detected by one of the multiple spectral imaging devices 209.

The plant height sensor 214 is configured to detect a height of an individual plant, or an average height of multiple plants. In one example, the plant height sensor 214 includes a LIDAR system that uses a light beam reflected by the plant to estimate its height. In another example, the plant height sensor 214 includes a binocular image capture system that captures two images of a plant from different perspectives and compares the two images to estimate the height of the plant based on a known offset position of the perspectives from which the images were captures.

The humidity sensor 215, the temperature sensor 216, and the barometric pressure sensor 217 are examples of meteorological sensors that can be included in the sensors 208. In other implementations, the sensors 208 include fewer meteorological sensors, more meteorological sensors, or different meteorological sensors. Further, the sensors 208 can include other sensors to gather information about specific portions of a crop field. The humidity sensor 215, the temperature sensor 216, the barometric pressure sensor 217, plant height sensor 214, the light meter 213, other sensors (if present), or a combination thereof, generate other data 221, which is provided to the data collection controller 130. The data collection controller 130 can use the other data 221 with the spectral imaging data 144 to schedule an agricultural activity. In one exemplary embodiment, the agricultural monitoring system can estimate a harvest date range for a crop field of a specific sugar cane variety, based on the collected sensor data, analysis of prior growth rates and the sensed crop height. In one exemplary embodiment, the agricultural monitoring system can estimate a harvest date range based on a sensed crop height for a particular sugar cane variety of at least 2 meters, for example, and present sensed crop growth rate as a percentage change in height that is less than a prior sensed crop growth rate (indicating that the crop growth rate may be slowing as crop nears maturity). In the exemplary embodiment, the crop may be a sugar cane variety such as RB 835486, RB 855536 or RB 855453, for example.

Figure 3:
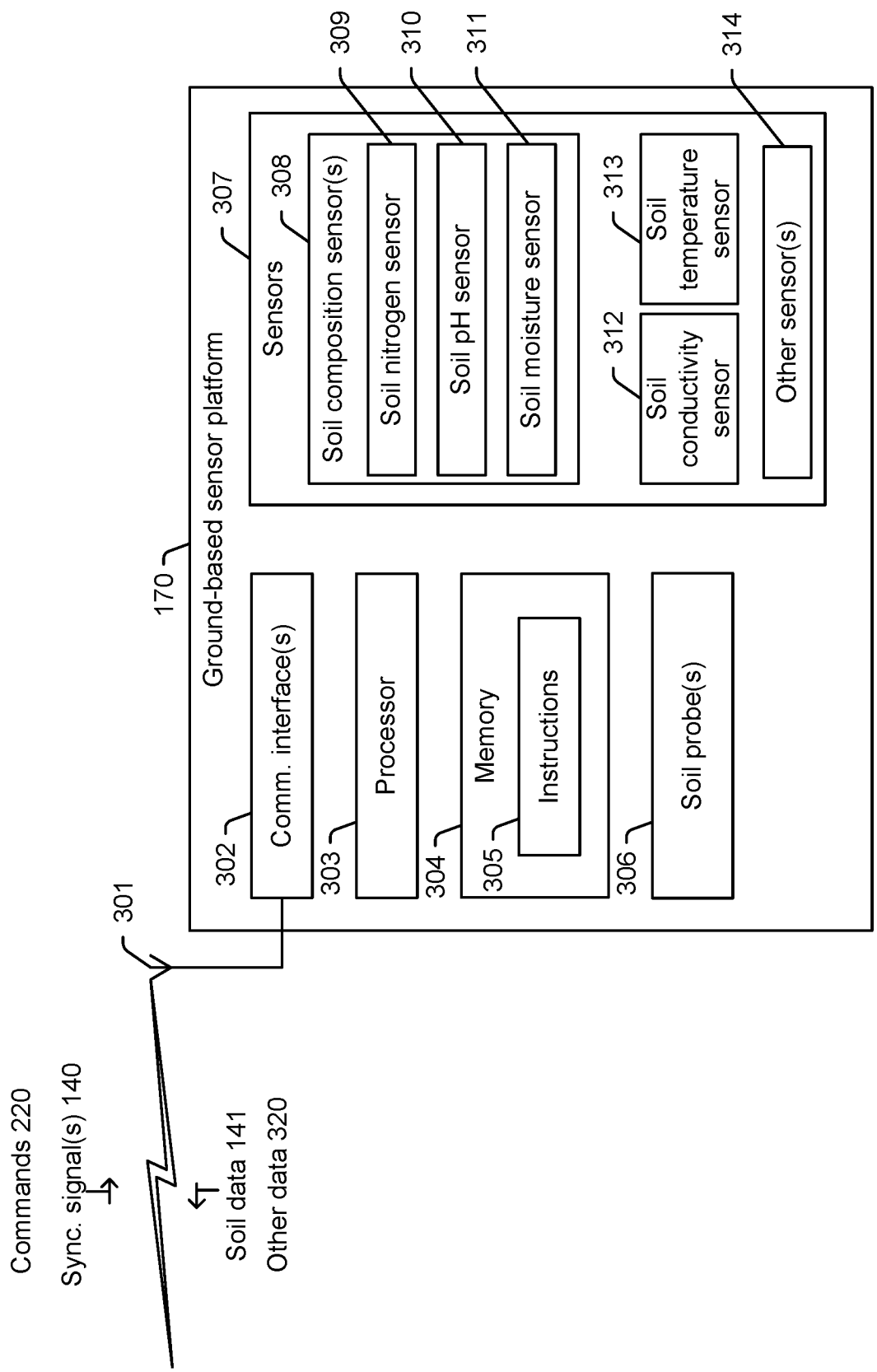
FIG. 3 is a block diagram that illustrates a ground-based sensor platform of the agricultural monitoring system of FIG. 1.

FIG. 3 is a block diagram that illustrates an example of the ground-based sensor platform 170 in further detail. In the example illustrated in FIG. 3, the ground-based sensor platform 170 includes a processor 303, a memory 304, one or more soil probes 306, a plurality of sensors 307, and one or more communication interfaces 302. In FIG. 3, the communication interfaces 302 include a wireless communication interface (e.g., including a transmitter and a receiver) coupled to an antenna 301. The communications interfaces 302 can also include a wired communication interface, such as a data port (e.g., a universal serial bus (USB) port, an Ethernet port, etc.).

The processor 303 is configured to execute instructions 305 stored in the memory 304 to control operation of the ground-based sensor platform 170. In some implementations, the processor 303 is also configured to perform one or more operations responsive to the synchronization signals 140 and the commands 220 received via the communications interfaces 302. For example, the commands 220 can direct that particular ones of the sensors 307 be used to gather data. For example, the commands 220 may direct the ground-based sensor platform 170 to use a soil temperature sensor 313 to generate the soil data 141.

In FIG. 3, the sensors 307 include one or more soil composition sensors 308, a soil conductivity sensor 312, and the soil temperature sensor 313. Further, in FIG. 3, the one or more soil composition sensors 308 include a soil nitrogen sensor 309, a soil pH sensor 310, and a soil moisture sensor 311. In other implementations, the sensors 307 include more sensors, fewer sensors, or different sensors. Further, in some implementations, two or more of the sensors 307 can be combined. For example, soil conductivity can be correlated with soil moisture content based on calibration data. Accordingly, in some implementations, the soil conductivity sensor 312 can be used to determine or estimate moisture content of the soil and no separate soil moisture sensor 311 is used. Further, in some implementations, the sensors 307 include other sensors 314 that are not specifically soil sensors. For example, the other sensor 314 can include meteorological sensors, such as the humidity sensor 215, the temperature sensor 216, and the barometric pressure sensor 217 of FIG. 2. As another example, the other sensors 314 can include meteorological sensors that generate data based on conditions between data collection periods (e.g., when the aerial sensor platform 180 may not be present). To illustrate, the other sensors 314 may include a rain gauge to generate data quantifying rainfall over a period of time. The data collection controller 130 may use the soil data 141 and the other data 320 to schedule an agricultural activity.

Figure 4A:
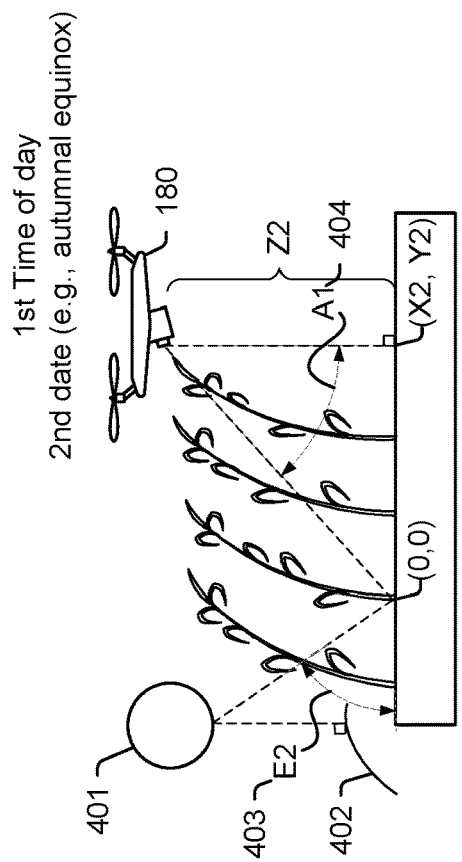
FIGS. 4A, 4B, 4C, and 4D are diagrams illustrating changes in solar angle between data collection periods and related effects on image capture positions.
Figure 4B:
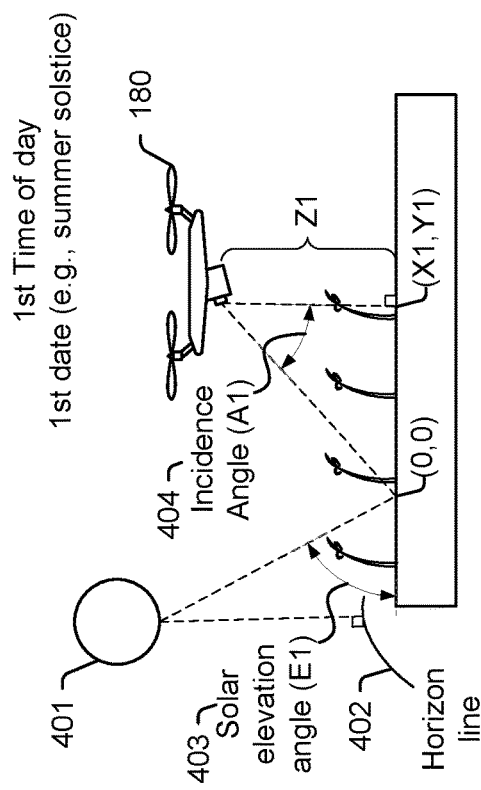
Figure 4C:
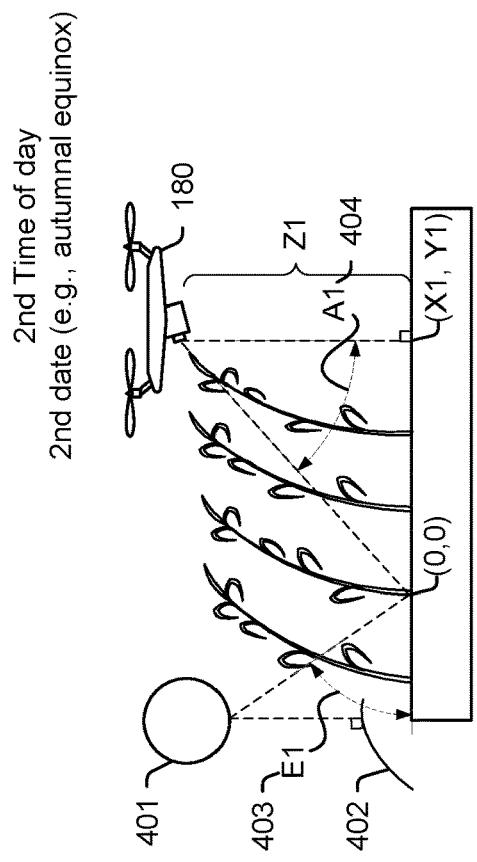
Figure 4D:
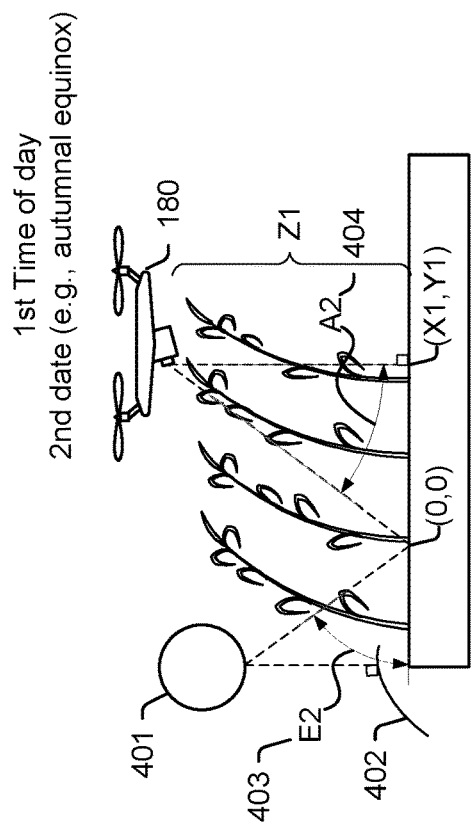

FIGS. 4A, 4B, 4C, and 4D are diagrams illustrating changes in solar angle between data collection periods and related effects on image capture positions. FIG. 4A illustrates capturing spectral imaging data during a first data collection period corresponding to a first time of day on a first date. FIGS. 4B, 4C, and 4D illustrate capturing spectral imaging data during a second data collection period that is subsequent to the first data collection period. In the particular examples illustrated in FIGS. 4A-4D, the first data collection period is on a date corresponding to the summer solstice (e.g., about June 21st) and the second data collection period is on a date corresponding to the autumnal equinox (e.g., about September 21st).

In FIG. 4A, during the first data collection period, a first image (or first spectral imaging data) is captured at a first time (e.g., 2 p.m.) while the aerial sensor platform 180 is over a first location (indicated by coordinates X1 and Y1) and at a first altitude (indicated by coordinate Z1). At the first time on the first date, an elevation angle of the sun 401 from the first location and first altitude corresponds to a first solar elevation angle 403. In this context, the solar elevation angle is an apparent angle of the bottom of the sun 401 above the horizon line 402 from a reference point (coordinates (0,0)) corresponding to a focal point of an imaging device of the aerial sensor platform 180. As shown in FIG. 4A, the solar elevation angle 403 has a first value, E1, and an incidence angle 404 of light from the reference point at the spectral imaging device of the aerial sensor platform 180 has a value A1. In this context, the incidence angle 404 refers to an angle between a first line extending between the reference point and the aerial sensor platform 180 and a second line corresponding to an altitude axis of the aerial sensor platform 180. Thus, the value A1 of the incidence angle 404 in FIG. 4A is related to the X, Y, and Z location of the aerial sensor platform 180, to the focal point of the spectral imaging device, and to the solar elevation angle 403.

For some spectral imaging techniques, comparison of two spectral images can be simplified by limiting changes in illumination in the two spectral images. Thus, programming or controlling the aerial sensor platform 180 to limit or reduce illumination changes can simplify or improve spectral image analysis. Illumination changes can be reduced by capturing spectral images in a manner that limits or reduces changes in solar angle from one sampling period (also referred to herein as a "data collection period") to the next.

FIG. 4B illustrates potential effects of taking a naïve approach to spectral image collection. In FIG. 4B, the aerial sensor platform 180 collects a spectral image from the first location (e.g., (X1, Y1)) and the first altitude (Z1) at the first time of day (e.g., 2 p.m.) on the second date (e.g., the autumnal equinox). On the second date at the first time of day, the solar elevation angle 403 has a value E2 that is not equal to E1. In particular, for the dates illustrated in FIGS. 4A and 4B, the solar elevation angle E2 is less than the solar elevation angle E2. As a result, the incidence angle 404 in FIG. 4B has a value A2, which is not equal to A1. Thus, taking the naïve approach of capturing spectral image data at the same time of day on each sampling date can lead to significant illumination differences between images, which can limit usefulness of some analytic techniques that compare images to identify differences.

FIGS. 4C and 4D illustrate improved techniques for spectral image collection. In each of FIGS. 4C and 4D, the aerial sensor platform 180 is programmed or controlled (e.g., by the data collection controller 130) to capture spectral imaging data in a manner that reduces illumination changes between various captured images.

In FIG. 4C, the location (X2, Y2) and/or elevation (Z2) of the aerial sensor platform 180 during spectral image collection on the second date is different from the first location (X1, Y1) and first elevation (Z1) of the aerial sensor platform 180 when the first spectral image was captured. In particular, the location and/or elevation for spectral image collection on the second date is selected such that the incidence angle 404 has the value A1 when the second image is captured. For example, the data collection controller 130 can calculate the value A1 of the incidence angle 404 for the first spectral image collected during the first sampling period and can schedule collection of the second spectral image on the second date at a location or elevation at which the incidence angle 404 will have the same value at the first time of day (based on the solar elevation angle 403). Thus, in FIG. 4C, the second image is collected at the same time of day as the first image, but from a slightly different location and/or elevation (e.g., at X2, Y2, Z2) than the first image.

In FIG. 4D, the time of day for spectral image collection on the second date is different from the first time of day at which the first spectral image was captured on the first date. In particular, the time of day for spectral image collection on the second date is selected such that the solar elevation angle 403 has the value E1 when the second image is captured. For example, the data collection controller 130 can calculate the value E1 of the solar elevation angle 403 for the first spectral image collected during the first sampling period and can schedule collection of the second spectral image on the second date at a time at which the sun 401 has the same solar elevation angle 403. Thus, in FIG. 4D, the second image is collected from the same location and elevation (e.g., at X1, Y1, Z1) as the first image, but is collected at a different time of day.

Figure 5:
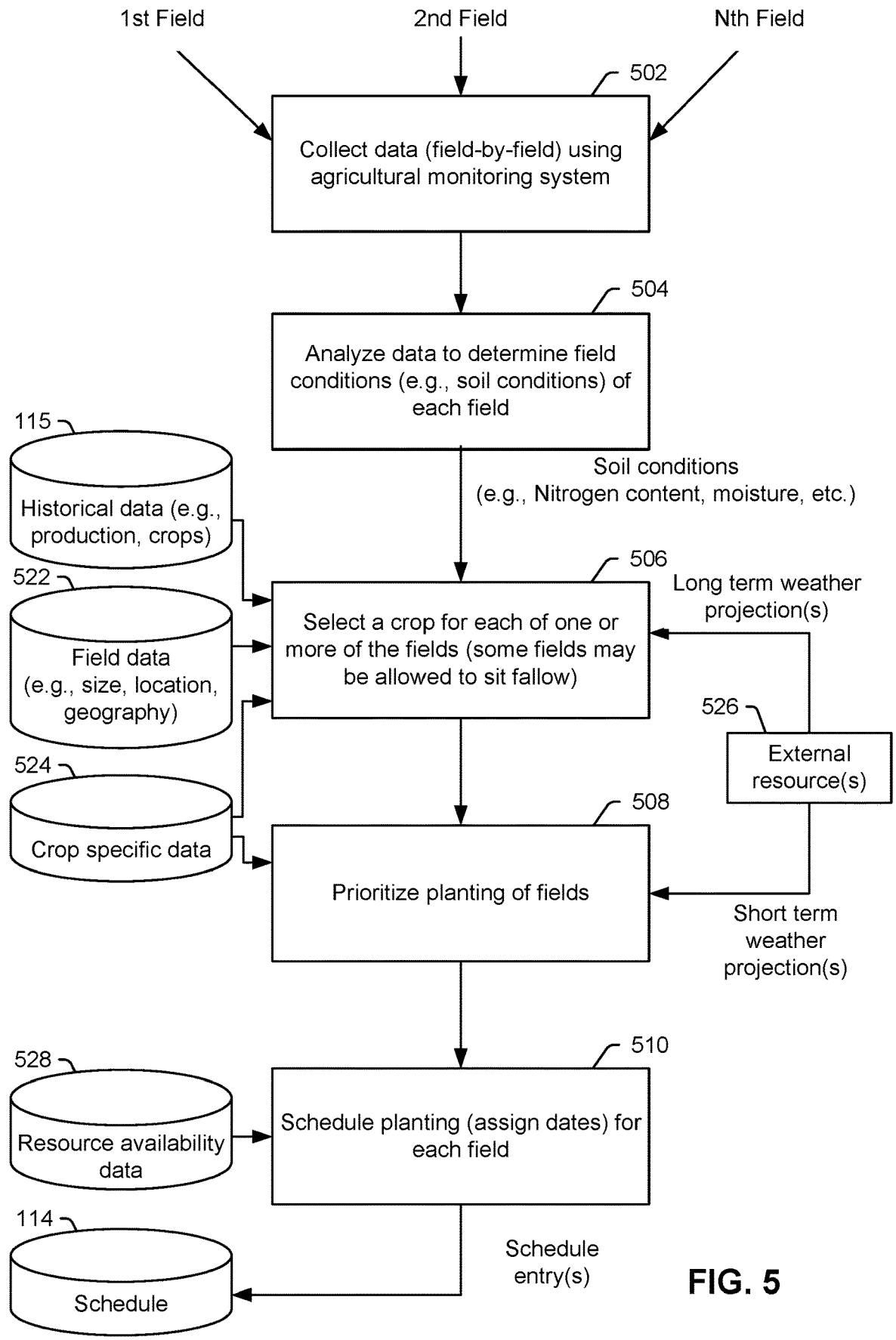
FIG. 5 is a flow chart of an example of a method of scheduling planting of crop fields based on data from the agricultural monitoring system of FIG. 1.

FIG. 5 is a flow chart of an example of a method of scheduling planting of crop fields based on data from the agricultural monitoring system 100 of FIG. 1. The operations illustrated in FIG. 5 can be performed by the data collection controller 130, the computing device 110, or a combination thereof. The agricultural monitoring system 100 is used, at 502, to gather data regarding a plurality of crop fields, including a first crop field, a second crop field, and an Nth crop field. The data is collected on a field-by-field basis such that data for the various fields can be analyzed individually, compared with other fields, etc. The data can be collected during a single data collection period or can be collected over a longer period of time that includes multiple data collection periods, such as over one or more seasons or one or more years.

The data for each field can be analyzed, at 504, to determine field conditions of each crop field. Analyzing the data can include determine current or real-time conditions, determining historical trends, projecting future conditions based on the historical trends and the current conditions, or a combination thereof. For example, based on the data, the current soil nitrogen content of a field, the current soil moisture content of the field, the condition of a crop currently in the field, indications of pests in the field, other field conditions, or a combination thereof, can be determined. As another example, based on the data, historical trends in the soil nitrogen content of the field, the soil moisture content of the field, the condition of a crop in the field, indications of pests in the field, other field conditions, or a combination thereof, can be determined. In this example, the historical trends and the current conditions can be used to estimate future conditions in the field.

Results of the analysis, such as the soil conditions, can be used, at 506, to select a crop for one or more of the fields. In some examples, one or more of the fields can be designated to sit fallow for a particular season, in which case no crop is selected for such fields. Additionally, if a particular field is already planted with a crop that is not scheduled to be harvested before the next round of planting, no crop is selected for that field. Among fields that are to be planted, each is assigned a crop. The crop assigned to each field is selected based on the historical data 115, data collected for the field (e.g., field data 522), crop specific data 524, and long-term weather projections (from an external resource 526). The crop specific data 524 includes information such as a market value (or market value projection) for each crop and growth characteristics for each crop. The growth characteristics indicate, for example, whether the crop is a nitrogen-binding crop, soil conditions under which the crop can grow or soil conditions to be avoided, common pests, and so forth.

As a specific example, a crop rotation process can be used to rotate planting nitrogen-consuming crops and nitrogen-binding crops in each field. Generally, such crop rotation processes are implemented using a simple counting process. To illustrate, a nitrogen-binding crop is planted after every fifth or sixth nitrogen-consuming crop is harvested. However, using the historical data 115, the field data 522, and the crop specific data 524, a crop rotation process that optimizes or improves output of each of multiple crop fields can be used. For example, current and historical conditions of each field can be analyzed to detect that nitrogen content of a particular field is being depleted faster than expected, and thus the particular field can be scheduled for planting of a nitrogen-binding crop earlier than would be expected using the simple count process. As another example, nitrogen-binding crops and nitrogen-consuming crops can flourish under somewhat different conditions. Thus, if soil or environmental conditions at a particular field are more suitable for a nitrogen-binding crop than for a nitrogen-consuming crop, planting of the nitrogen-binding crop can be performed earlier than would be expected using the simple count process.

After crops to be planted have been selected, an order of planting of each of the fields is determined by prioritizing the planting of the fields, at 508. In the example illustrated in FIG. 5, planting of the crops is prioritized based on the crop specific data 524 and short-term weather projections. In this example, the crop specific data 524 includes information about planting conditions associated with each crop, such as preferred soil conditions, field preparation requirements (e.g., fertilization, plowing, etc.), and so forth. The short-term weather projections indicate, for example, temperature and precipitation projections. The short-term weather projections and the crop specific data 524 can be used to estimate when each field will be ready to plant (e.g., when weather and field conditions will be acceptable for planting). Planting of the fields can be prioritized based on the estimate of when each field will be ready to plant and based on criticality of various planting conditions. For example, a first crop selected for a first field and a second crop selected for a second field may both prefer moist soil upon planting. If the fields are close to one another, the soil moisture content of the both fields may vary with rainfall in the area. If there is only time to plant one crop after a rain, the historical data 115 can be used to determine how critical moist soil is to each crop (based on past production under various planting conditions) and the criticality of soil moisture to each crop can be used to prioritize planting of one crop ahead of the other.

After a priority order of planting of the crops is determined, the priority order of planting can be used to schedule planting of each field, at 510. The priority order of planting can be used in conjunction with other information, such as resource availability data 528 to schedule the planting. The resource availability data 528 can indicate availability of agricultural equipment, personnel, supplies (e.g., seeds, fertilizer), etc. Scheduling is based on the priority order of planting and resource availability. For example, if two fields are to be prepared using a particular process and only one piece of agricultural equipment is available to perform the process, whichever of the fields has the higher priority is scheduled to use the piece of agricultural equipment before the other field. Scheduling the planting of the fields results in generation of one or more schedule entries, which are added to the schedule 114 to regulate or control distribution of assets to conduct the planting.

Figure 6:
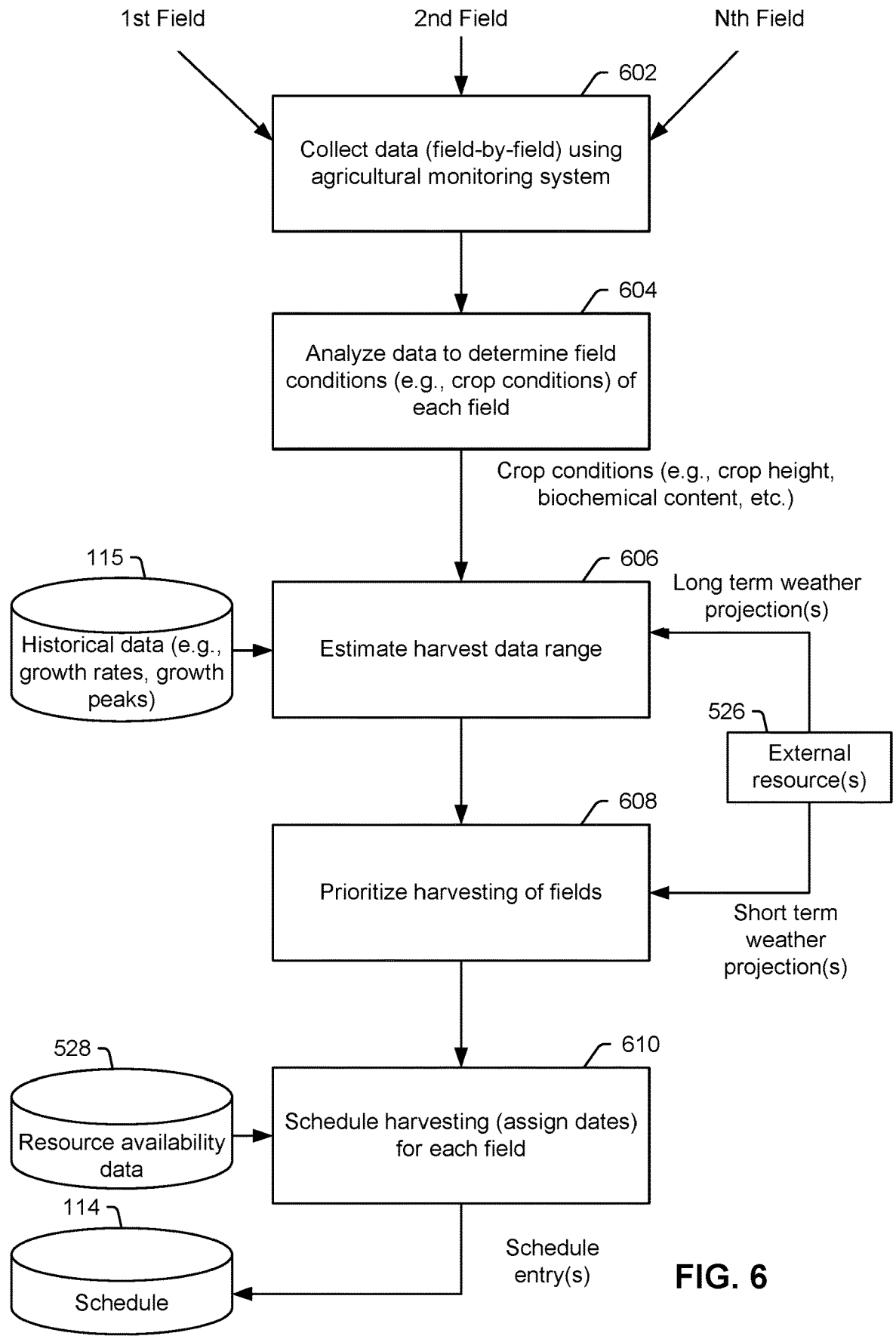
FIG. 6 is a flow chart of an example of a method of scheduling harvesting of crop fields based on data from the agricultural monitoring system of FIG. 1.

FIG. 6 is a flow chart of an example of a method of scheduling harvesting of crop fields based on data from the agricultural monitoring system of FIG. 1. The operations illustrated in FIG. 6 can be performed by the data collection controller 130, the computing device 110, or a combination thereof. The agricultural monitoring system 100 is used, at 602, to gather data regarding a plurality of crop fields, including a first crop field, a second crop field, and an Nth crop field. The data is collected on a field-by-field basis such that data for the various fields can be analyzed individually, compared with other fields, etc. The data can be collected during a single data collection period or can be collected over a longer period of time that includes multiple data collection periods, such as over one or more seasons or one or more years.

The data for each field can be analyzed, at 604, to determine field conditions (including crop conditions) of each crop field. Crop conditions can include, for example, crop height, presence of a particular biochemical, quantification of the particular biochemical, etc. Analyzing the data can include determine current or real-time conditions, determining historical trends, projecting future conditions based on the historical trends and the current conditions, or a combination thereof. For example, based on the data, the plant height, a quantity of a target chemical, indications of pests in the field, other crop conditions, or a combination thereof, can be determined. As another example, based on the data, historical trends in the plant height, the quantity of the target chemical, indications of pests in the field, other crop conditions, or a combination thereof, can be determined. In this example, the historical trends and the current conditions can be used to estimate future conditions of the crop.

Results of the analysis, such as the crop conditions, can be used, at 606, to estimate a harvest date range for each crop. In the example illustrated in FIG. 6, the harvest data range for each crop is estimated based on the historical data 115, the crop conditions, and long-term weather projections (from the external resource 526). The historical data 115 includes information such as historical growth rates or growth rate trends, historical growth peaks, etc. To illustrate, the historical data 115 may indicate, for a particular crop, that on average a first chemical species is present in a particular quantity at harvesting and that the quantity of the first chemical species has been changing at a first rate during recent data collection periods. The rate of change of the quantity of the first chemical species can be used with the current crop conditions to estimate the harvest date range to coincide with a time when the crop will reach the peak harvesting quantity of the first chemical species.

The harvest data range can also account for the long-term weather projections. To illustrate, if a period of unusually wet weather is projected to occur in several weeks, the harvest date range for one or more crops may be move earlier in time than would be indicated by the historical data and crop conditions alone to avoid possible crop damage due to rain or to avoid increased time and expense of harvesting in rain. Conversely, if the crop can experience a significant growth spurt due to near harvest rainfall, harvesting of the crop can be delayed past a time indicated by the historical data and crop conditions alone to take advantage of the beneficial rainfall.

After the harvest data range for each crop has been estimated, harvesting of each of the fields is prioritized, at 608. In the example illustrated in FIG. 6, harvesting of the fields is prioritized based on short-term weather projections. In some implementations the historical data 115, the field data 522, the crop specific data 524, or other data is used in conjunction with the short-term weather projections to prioritize the harvesting. The short-term weather projections can be used to assign harvesting priorities to fields based on how the forecasted weather is expected to favorably or unfavorably affect the crop in each field.

After a priority order of harvesting of the crops is determined, the priority order of harvesting can be used to schedule harvesting of the each field, at 610. The priority order of harvesting can be used in conjunction with other information, such as the resource availability data 528 to schedule the harvesting. For example, if two fields will be ready to harvest in a specific harvest date range and each is to be harvested using a particular piece of agricultural equipment, whichever of the fields has the higher harvesting priority is scheduled to use the piece of agricultural equipment before the other field. Scheduling the harvesting of the fields results in generation of one or more schedule entries, which are added to the schedule 114 to regulate or control distribution of assets to conduct the harvesting.

Figure 7:
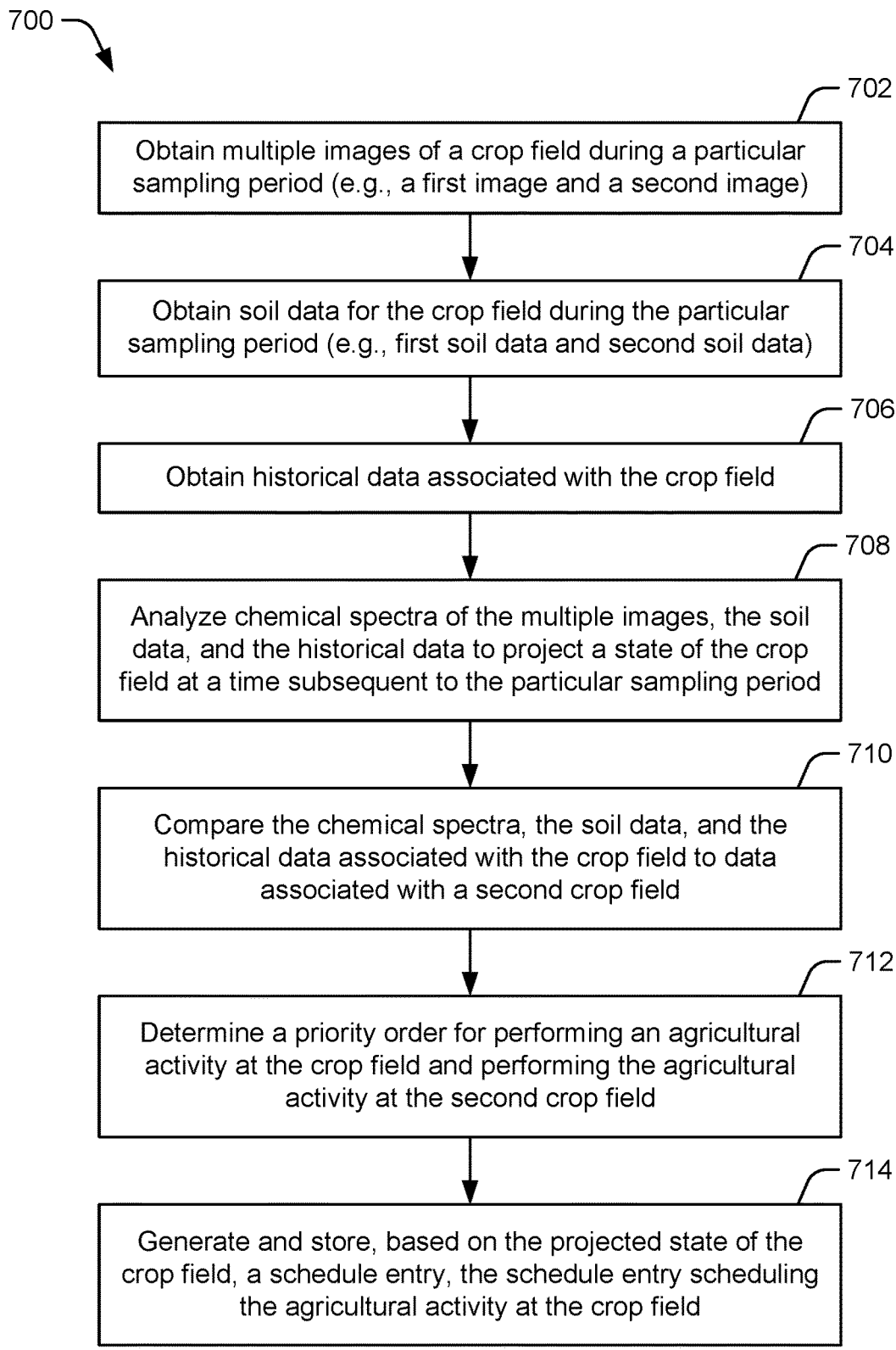
FIG. 7 is a flow chart of an example of a method of monitoring biofuel feedstock crops using the agricultural monitoring system of FIG. 1.

FIG. 7 is a flow chart of an example of a method 700 of monitoring biofuel feedstock crops using the agricultural monitoring system 100 of FIG. 1. The operations illustrated in FIG. 7 can be performed by the data collection controller 130, the computing device 110, or a combination thereof.

The method 700 includes, at 702, obtaining multiple images, each image of the multiple images collected by a spectral imaging device of an aerial sensor platform during a particular sampling period. The multiple images include a first image representing a first field of view of a first geographic region of a crop field and a second image representing a second field of view of a second geographic region of the crop field. For example, the aerial sensor platform 180 of FIG. 1 can capture a first image representing a first field of view of the first geographic region 151 of the first crop field 150 and can capture a second image representing a second field of view of the second geographic region 152 of the first crop field 150. The first image and the second image can be transmitted to the data collection controller 130 as part of the spectral imaging data 144.

The method 700 also includes, at 704, obtaining soil data collected by multiple ground-based sensor platforms during the particular sampling period. The soil data includes first soil data associated with the first geographic region and second soil data associated with the second geographic region. To illustrate, continuing the example above, a first ground-based sensor platform in the first geographic region 151 of the first crop field 150 can capture the first soil data and a second ground-based sensor platform in the second geographic region 152 of the first crop field 150 can capture the second soil data. In some implementations, capturing soil data and capturing spectral imaging data is synchronized. For example, the aerial sensor platform 180 can capture the first image and the first ground-based sensor platform can capture the first soil data in response to the synchronization signals 140 from the data collection controller 130.

The method 700 further includes, at 706, obtaining historical data associated with the crop field. For example, the data collection controller 130 can provide the spectral imaging data 144 and the soil data 141 to the computing device 110 of FIG. 1, and the computing device 110 can access the historical data 115 from the memory 112. The method 700 also includes, at 708, analyzing chemical spectra of the multiple images, the soil data, and the historical data to project a state of the crop field at a time subsequent to the particular sampling period. For example, the chemical spectra can be analyzed to estimate a quantity of a target chemical (such as a sugar) represented in the spectral imaging data. In this example, the computing device 110 can project a future biochemical content associated with the crop field based on the current biochemical content, the soil data 141, and the historical data 115. To illustrate, the historical data 115 can be analyzed to identify a historical trend that indicates a particular growth rate or a particular rate of change of the target chemical (e.g., a ripening rate) of the crop under particular circumstances, such as with particular soil nitrogen content levels, particular soil water content, etc.

In the implementation illustrated in FIG. 7, the method 700 includes, at 710, comparing the chemical spectra, the soil data, and the historical data associated with the crop field to data associated with a second crop field, and, at 712, determining a priority order for performing agricultural activities at the crop field and the second crop field. For example, as described with reference to FIG. 6, an order of harvesting crops in the first crop field 150 and the second crop field 160 of FIG. 1 can be determined based on the spectral imaging data 144, the soil data 141, and the historical data 115. As another example, as described with reference to FIG. 5, an order of planting particular crops in the first crop field 150 and the second crop field 160 of FIG. 1 can be determined based on the spectral imaging data 144, the soil data 141, and the historical data 115.

The method 700 includes, at 714, generating and storing, based on the projected state of the crop field (and the priority order in some implementations), a schedule entry, where the schedule entry schedules an agricultural activity at the crop field. For example, the computing device 110 generates the schedule entry 119 and stores the schedule entry 119 in the memory 112 as part of the schedule 114. The computing device 110 can also display the schedule entry 119 or use the schedule entry 119 for another purpose, such as automatically requisitioning equipment or supplies to meet the schedule 114.

In some implementations, the method 700 further includes determining, based on the chemical spectra and the soil data, a nitrogen fixation state associated with the crop field. In such implementations, a particular crop to be planted in the crop field can be selected based on the nitrogen fixation state. Further, a range of planting dates of the particular crop can be determined based at least in part on the historical data. In such implementations, the schedule entry identifies the particular crop and at least one date within the range of planting dates.

Although one or more of FIGS. 1-7 illustrate systems, apparatuses, and/or methods according to the teachings of the disclosure, the disclosure is not limited to these illustrated systems, apparatuses, and/or methods. One or more functions or components of any of FIGS. 1-7 as illustrated or described herein may be combined with one or more other portions of another of FIGS. 1-7. For example, one or more elements of the method 500 of FIG. 5, the method 600 of FIG. 6, the method 700 of FIG. 7, or a combination thereof, can be performed in combination with one or more elements of another of the method 500 of FIG. 5, the method 600 of FIG. 6, the method 700 of FIG. 7, or with other operations described herein. Accordingly, no single implementation described herein should be construed as limiting and implementations of the disclosure may be suitably combined without departing form the teachings of the disclosure. As an example, one or more operations described with reference to FIGS. 5-7 may be optional, may be performed at least partially concurrently, and/or may be performed in a different order than shown or described.

The illustrations of the examples described herein are intended to provide a general understanding of the structure of the various implementations. The illustrations are not intended to serve as a complete description of all of the elements and features of apparatus and systems that utilize the structures or methods described herein. Many other implementations may be apparent to those of skill in the art upon reviewing the disclosure. Other implementations may be utilized and derived from the disclosure, such that structural and logical substitutions and changes may be made without departing from the scope of the disclosure. For example, method operations may be performed in a different order than shown in the figures or one or more method operations may be omitted. Accordingly, the disclosure and the figures are to be regarded as illustrative rather than restrictive.

Moreover, although specific examples have been illustrated and described herein, it should be appreciated that any subsequent arrangement designed to achieve the same or similar results may be substituted for the specific implementations shown. This disclosure is intended to cover any and all subsequent adaptations or variations of various implementations. Combinations of the above implementations, and other implementations not specifically described herein, will be apparent to those of skill in the art upon reviewing the description.

The Abstract of the Disclosure is submitted with the understanding that it will not be used to interpret or limit the scope or meaning of the claims. In addition, in the foregoing Detailed Description, various features may be grouped together or described in a single implementation for the purpose of streamlining the disclosure. Examples described above illustrate but do not limit the disclosure. It should also be understood that numerous modifications and variations are possible in accordance with the principles of the present disclosure. As the following claims reflect, the claimed subject matter may be directed to less than all of the features of any of the disclosed examples. Accordingly, the scope of the disclosure is defined by the following claims and their equivalents.

What is claimed is:

1. An agricultural monitoring system for monitoring biofuel feedstock crops, the agricultural monitoring system comprising:
   an aerial sensor platform comprising a spectral imaging device, a position sensor, and an orientation sensor;
   a ground-based sensor platform comprising at least one soil sensor; and
   a computing device comprising a processor and a memory storing instructions that are executable by the processor to:
      determine a first incidence angle associated with previously captured spectral imaging data collected by the spectral imaging device focused on a focal point, the previously captured spectral imaging data collected at a first time on a first day and representing a particular field of view of a particular geographic region of a crop field, the particular geographic region determined based on position data from the position sensor and the particular field of view determined based on orientation data from the orientation sensor;
      move the aerial sensor platform to a particular position having substantially the same field of view as the particular field of view on a second day different than the first day to take second spectral imaging data;
      focus the spectral imaging device on the focal point;
      capture the second spectral imaging data at the first time on the second day from the particular position, wherein particular position is selected to cause a second incidence angle associated with the second spectral imaging data to be substantially the same as the first incidence angle;
      obtain first soil data collected by the at least one soil sensor, the at least one soil sensor associated with the particular geographic region;
      estimate a quantity of a biochemical compound in a crop in the crop field based on the previously captured spectral imaging data and the second spectral imaging data;
      estimate a future quantity of the biochemical compound in the crop in the crop field based on the quantity, the first soil data, and historical data; and
      schedule an agricultural activity for the crop field based on the future quantity of the biochemical compound.

2. The agricultural monitoring system of claim 1, further comprising:
   a transmitter; and
   a data collection controller coupled to the transmitter, the data collection controller configured to cause the transmitter to transmit at least one first signal to the aerial sensor platform and to the ground-based sensor platform to synchronize data collection by the at least one soil sensor and the spectral imaging device.

3. The agricultural monitoring system of claim 2, further comprising a receiver coupled to the data collection controller, the receiver configured to receive, responsive to the at least one first signal, the second spectral imaging data from the aerial sensor platform and the first soil data from the ground-based sensor platform.

4. The agricultural monitoring system of claim 3, wherein:
   the data collection controller is configured to cause the transmitter to transmit the at least one first signal during a first sampling period,
   the data collection controller is further configured to cause the transmitter to transmit at least one second signal to the aerial sensor platform and to the ground-based sensor platform during a second sampling period that is subsequent to the first sampling period,
   the receiver is configured to receive, responsive to the at least one second signal, third spectral imaging data collected by the spectral imaging device and second soil data collected by the soil sensor,
   the data collection controller is configured to generate sets of synchronized sample data, the sets of synchronized sample data including:
      a first set of synchronized sample data including the second spectral imaging data and the first soil data, and
      a second set of synchronized sample data including the third spectral imaging data and the second soil data, and the computing device is configured to obtain the second spectral imaging data and the first soil data from the sets of synchronized sample data.

5. The agricultural monitoring system of claim 4, wherein each set of synchronized sample data of the sets of synchronized sample data includes information indicating a date and time of data capture and a location of each sensor that captured data in the set.

6. The agricultural monitoring system of claim 2, wherein the data collection controller is configured to cause the transmitter to transmit the at least one first signal based on a determination of a location of the aerial sensor platform.

7. The agricultural monitoring system of claim 1, wherein collection of spectral imaging data based on the first incidence angle enables comparison of data taken in different seasons of a year.

8. The agricultural monitoring system of claim 1, wherein the spectral imaging device includes a multispectral image sensor or a hyperspectral image sensor.

9. The agricultural monitoring system of claim 1, wherein the aerial sensor platform further comprises a plant height sensor.

10. The agricultural monitoring system of claim 1, wherein the aerial sensor platform further comprises a light meter, a temperature sensor, a humidity sensor, a barometric pressure sensor, or a combination thereof.

11. The agricultural monitoring system of claim 1, wherein the at least one soil sensor comprises a soil composition sensor, a soil nitrogen sensor, a soil pH sensor, a soil moisture sensor, a soil temperature sensor, a soil conductivity sensor, or a combination thereof.

12. The agricultural monitoring system of claim 1, wherein the computing device includes a communication interface configured to access a network resource to obtain meteorological data regarding the particular geographic region, geological data regarding the particular geographic region, hydrological data regarding the particular geographic region, astronomical data regarding a data collection period, or a combination thereof.

13. The agricultural monitoring system of claim 1, wherein the biochemical compound comprises one or more sugars.

14. The agricultural monitoring system of claim 1, wherein the instructions are executable by the processor to cause the processor to:
obtain third spectral imaging data collected by the spectral imaging device, the third spectral imaging data representing a second crop field; and
obtain second soil data associated with the second crop field, wherein scheduling the agricultural activity includes prioritizing planting or harvesting of the crop field ahead of planting or harvesting of the second crop field.

15. The agricultural monitoring system of claim 1, wherein scheduling the agricultural activity includes selecting a particular crop to plant in the crop field from among a plurality of candidate crops.

16. A method for monitoring biofuel feedstock crops, the method comprising:
determining, at a data collection controller, a position and an orientation of an aerial sensor platform relative to a crop field at a first time when the aerial sensor platform collected previously captured spectral imaging data by a spectral imaging device on a first day, an incidence angle associated with the previously captured spectral imaging data, and a second time to collect second spectral imaging data on a second day by the spectral imaging device so that the second spectral imaging data is associated with the incidence angle;
sending position data from the data collection controller to the aerial sensor platform to cause the aerial sensor platform to move to the position and the orientation on the second day;
transmitting, from the data collection controller to the aerial sensor platform and to a ground-based sensor platform associated with the crop field, at least one synchronization signal to synchronize data collection by the spectral imaging device and by a soil sensor of the ground-based sensor platform;
receiving, at the data collection controller from the aerial sensor platform and from the ground-based sensor platform responsive to the at least one synchronization signal, the second spectral imaging data and second soil data from the soil sensor;
generating, at the data collection controller, a set of synchronized sample data including the soil data and the second spectral image data;
estimating a quantity of a biochemical compound in a crop in the crop field based on the second spectral imaging data obtained from the set;
estimating a future quantity of the biochemical compound in the crop in the crop field based on the quantity, the soil data, and historical data; and
generating and storing a schedule entry, the schedule entry scheduling an agricultural activity at the crop field based on the future quantity.

17. The method of claim 16, further comprising:
determining a nitrogen fixation state associated with the crop field;
selecting a particular crop to be planted in the crop field based on the nitrogen fixation state; and
selecting a range of planting dates of the particular crop based at least in part on the historical data, wherein the schedule entry identifies the particular crop and at least one date within the range of planting dates.

18. The method of claim 16, further comprising:
comparing a chemical spectra obtained from the sets of synchronized sample data and the historical data associated with the crop field to corresponding data associated with a second crop field; and
determining a priority order for performing the agricultural activity at the crop field and for performing the agricultural activity at the second crop field based on a comparison of the chemical spectra, wherein the schedule entry is based on the priority order.

19. An agricultural monitoring system for monitoring biofuel feedstock crops, the agricultural monitoring system comprising:
a transmitter;
a receiver; and
a data collection controller coupled to the transmitter and to the receiver, the data collection controller comprising a processor and a memory, the memory storing instructions that are executable by the processor to cause the data collection controller to:
determine a position and an orientation of an aerial sensor platform relative to a crop field at a first time when the aerial sensor platform collected previously captured spectral imaging data by a spectral imaging device on a first day, an incidence angle associated with the previously captured spectral imaging data, and a second time to collect second spectral imaging data by the spectral imaging device on a second day so that the second spectral imaging data is associated with the incidence angle, wherein the position is determined from position data received from the aerial sensor platform and the orientation is determined from orientation data received from the aerial sensor platform;

move the aerial sensor platform to the position and the orientation on the second day;

cause the transmitter to transmit, to the aerial sensor platform and to a ground-based sensor platform, at least one signal to synchronize data collection by the spectral imaging device and by a soil sensor of the ground-based sensor platform;

receive, via the receiver from the aerial sensor platform and the ground-based sensor platform responsive to the at least one signal, the second spectral imaging data and soil data from the soil sensor;

generate a set of synchronized sample data including the soil data and the second spectral image data;

store the set of synchronized sample data in the memory;

estimate a quantity of a biochemical compound in a crop in the crop field based on the second spectral imaging data from the set;

estimate a future quantity of the biochemical compound in the crop in the crop field based on the quantity, the soil data, and historical data; and schedule an agricultural activity for the crop field based on the future quantity of the biochemical compound.

20. The agricultural monitoring system of claim 19, wherein the instructions, when executed by the processor, further cause the data collection controller to:

receive, via the receiver on the second day, second position data and second orientation data from the aerial sensor platform; and transmit a particular signal to the aerial sensor platform based on the second position data and the second orientation data indicating that the aerial sensor platform is at the position and the orientation.

* * * * *

UNITED STATES PATENT AND TRADEMARK OFFICE
CERTIFICATE OF CORRECTION

PATENT NO. : 10,937,148 B2  
APPLICATION NO. : 15/871758  
DATED : March 2, 2021  
INVENTOR(S) : Marcio Pupin Mello It is certified that error appears in the above-identified patent and that said Letters Patent is hereby corrected as shown below:

In the Claims

Claim 16, Column 24, Line 16 after "data and" delete "second".

Signed and Sealed this
Eighteenth Day of May, 2021

Drew Hirshfeld
*Performing the Functions and Duties of the*
*Under Secretary of Commerce for Intellectual Property and*
*Director of the United States Patent and Trademark Office*